(12) United States Patent
Kapur et al.

(10) Patent No.: US 12,278,002 B2
(45) Date of Patent: Apr. 15, 2025

(54) TRIGGERING VIRTUAL CLINICAL EXAMS

(71) Applicant: Verily Life Sciences LLC, South San Francisco, CA (US)

(72) Inventors: Ritu Kapur, San Francisco, CA (US); Maximilien Burq, Mountain View, CA (US); Erin Rainaldi, San Francisco, CA (US); Lance Jonathan Myers, Pacifica, CA (US); William Marks, San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 477 days.

(21) Appl. No.: 17/450,521

(22) Filed: Oct. 11, 2021

(65) Prior Publication Data
US 2022/0115096 A1   Apr. 14, 2022

Related U.S. Application Data

(60) Provisional application No. 63/198,335, filed on Oct. 12, 2020.

(51) Int. Cl.
*G16H 10/20* (2018.01)
*G06Q 10/1093* (2023.01)
*G16H 40/20* (2018.01)

(52) U.S. Cl.
CPC ......... *G16H 10/20* (2018.01); *G06Q 10/1097* (2013.01); *G16H 40/20* (2018.01)

(58) Field of Classification Search
CPC ........ G16H 10/20; G16H 40/20; G16H 10/60; G16H 40/63; G16H 40/67; G16H 50/20; G16H 50/70; G06Q 10/1097
See application file for complete search history.

(56) References Cited

U.S. PATENT DOCUMENTS

| | | | |
|---|---|---|---|
| 2008/0275913 A1 | 11/2008 | Van Arragon et al. | |
| 2009/0248442 A1 | 10/2009 | Pacheco et al. | |
| 2015/0046183 A1* | 2/2015 | Cireddu | G16H 40/67 705/3 |
| 2017/0061074 A1* | 3/2017 | Singh | G16H 10/60 |
| 2019/0231262 A1* | 8/2019 | Nasry | G16H 80/00 |

OTHER PUBLICATIONS

"8 smart Parkinson's apps you need to try", Parkinson's Life, <parkinsonslife.eu/top-apps-for-the-parkinsons-community/>, Apr. 14, 2015.
"Use the Workout app on your Apple Watch", <https://support.apple.com/en-us/HT204523>, accessed May 22, 2020.
Aghanavesi et al., "A smartphone-based system to quantify dexterity in Parkinson's disease patients", Informatics in Medicine Unlocked 9 (2017): 11-17.
Prince et al., "Big data in Parkinson's disease: using smartphones to remotely detect longitudinal disease phenotypes", Physiological measurement 39.4 (2018): 044005.

\* cited by examiner

*Primary Examiner* — Meredith A Long
(74) *Attorney, Agent, or Firm* — Kilpatrick Townsend & Stockton LLP

(57) ABSTRACT

Triggering information that defines conditions for presenting a virtual clinical exam may be downloaded to a user device. The user device may collect sensor data and use the sensor data to evaluate the conditions. When certain conditions are fulfilled, the user device may present the virtual clinical exam at the user device.

20 Claims, 8 Drawing Sheets

| Data Types | Ranges | Thresholds |
|---|---|---|
| Dynamic sensor data 1 | DSD range 1 | DSD threshold 1 |
| Dynamic sensor data 2 | DSD range 2 | DSD threshold 2 |
| Dynamic sensor data N | DSD range N | DSD threshold N |
| Static data 1 | SD range 1 | SD threshold 1 |
| Static data 2 | SD range 2 | SD threshold 2 |
| Static data N | SD range N | SD threshold N |

TRIGGERING VIRTUAL CLINICAL EXAMS

CROSS-REFERENCE TO RELATED APPLICATIONS

This application claims priority to U.S. Provisional Patent Application No. 63/198,335, filed Oct. 12, 2020, titled "Triggering Virtual Clinical Exams," the entirety of which is hereby incorporated by reference.

BACKGROUND

Exams that test motor function of users have traditionally been conducted by clinicians in controlled clinical environments. Collecting data associated with these exams outside of this environment may be negatively impacted by external forces.

BRIEF SUMMARY

Various examples are described including systems, methods, and devices relating to triggering and presenting virtual clinical exams.

A system of one or more computers can be configured to perform particular operations or actions by virtue of having software, firmware, hardware, or a combination of them installed on the system that in operation cause the system to perform the actions. One or more computer programs can be configured to perform particular operations or actions by virtue of including instructions that, when executed by data-processing apparatus, cause the apparatus to perform the actions. One general aspect includes a computer-implemented method that includes receiving triggering information defining one or more conditions for triggering presentation of a virtual clinical exam at a user device. The computer-implemented method also includes receiving, from one or more sensors, dynamic sensor data corresponding to multimodal physiological signals associated with a user of the user device. The computer-implemented method also includes determining fulfillment of at least one condition of the one or more conditions based at least in part on a portion of the dynamic sensor data. The computer-implemented method also includes causing presentation of the virtual clinical exam at the user device based at least in part on determining fulfillment of at least one condition. The computer-implemented method also includes receiving, from the one or more sensors, further data associated with the virtual clinical exam. The computer-implemented method also includes determining and outputting results of the virtual clinical exam based on the further data. Other embodiments of this aspect include corresponding computer systems, apparatus, and computer programs recorded on one or more computer storage devices, each configured to perform the actions of the methods.

Another general aspect includes a computer-implemented method that includes receiving from a plurality of user devices exam information corresponding to a plurality of virtual clinical exams performed by the plurality of user devices. The exam information may identify at least a virtual clinical exam type for each of the plurality of virtual clinical exams. The computer-implemented method also includes receiving from the plurality of user devices dynamic sensor data corresponding to the plurality of virtual clinical exams, the dynamic sensor data collected by one or more sensors of the plurality of user devices. The computer-implemented method also includes determining one or more conditions for triggering presentation of a particular type of virtual clinical exam based at least in part on the exam information and the dynamic sensor data. The computer-implemented method also includes providing the one or more conditions to a particular user device for use by the particular user device in triggering presentation of the particular type of virtual clinical exam at the particular user device. Other embodiments of this aspect include corresponding computer systems, apparatus, and computer programs recorded on one or more computer storage devices, each configured to perform the actions of the methods.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
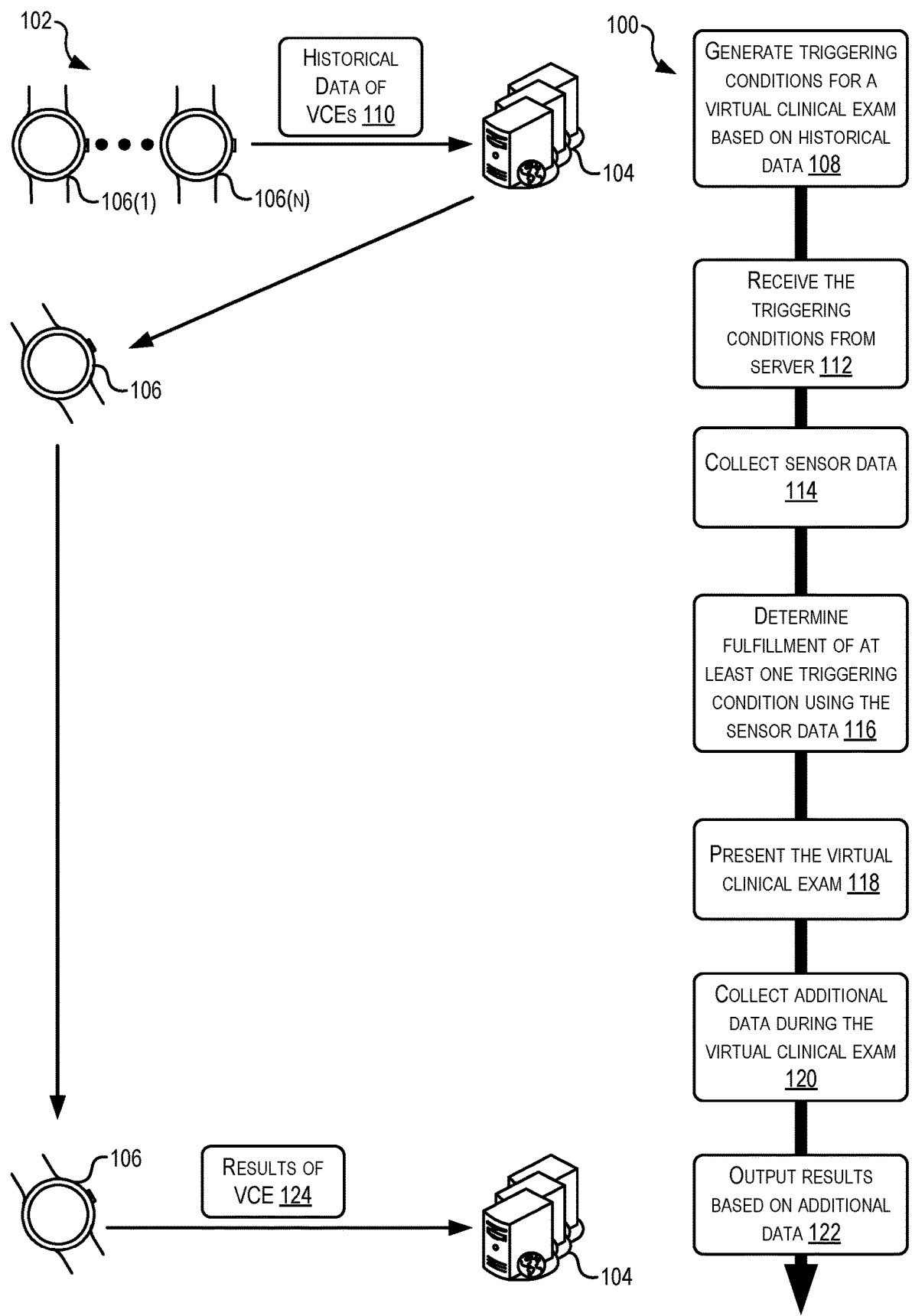
FIG. 1 illustrates a block diagram and a corresponding flowchart illustrating a process for triggering presentation of virtual clinical exams, according to at least one example.

Examples are described herein in the context of triggering and conducting virtual clinical exams on wearable user devices such as watches. Those of ordinary skill in the art will realize that the following description is illustrative only and is not intended to be in any way limiting. For example, although the techniques are described herein with respect to virtual clinical exams for purposes of assessing motor function, the techniques can also be used to trigger different types of exams, prompts, suggestions, and the like and may, in some examples, be implemented on non-wearable user devices, which may or may not be portable. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made to achieve the developer's specific goals, such as compliance with application- and business-related constraints, and that these specific goals will vary from one implementation to another and from one developer to another.

Parkinson's disease and other neurological disorders may cause motor dysfunction. Conventionally, a trained clinician will conduct a motor examination at a clinic or in a patient's home to help determine whether the patient's symptoms are related to a certain motor disorder, such as Parkinson's disease, and to also track progression of diseases. For example, during a physical examination such as an exam for assessing Parkinson's symptom severity, the clinician will look at tremor (e.g., repetitive movement caused by involuntary contractions of muscles), rigidity (e.g., stiffness in arms or legs), bradykinesia or akinesia (e.g., slowness of movement and/or lack of movement during regular tasks), and postural instability (e.g., balance issues). In some examples, at least some of the examination may be based on the Movement Disorder Society Unified Parkinson's Disease Rating Scale (MDS-UPDRS). Conducting conventional motor exams in such a controlled environment (e.g., by the trained clinician in the clinician's office) ensures collection of trusted data under suitable conditions. Unfortunately, conducting motor exams in the controlled environment is also costly and time consuming and limits the number of tests that can practically be conducted because of the limited availability of trained clinicians. The necessity of an in-clinic visit also excludes those who are unable to travel due to logistical constraints (e.g. distance from neurologist's office), severity of disease, or for reasons of safety (e.g. infectious disease pandemic).

Unlike conventional approaches for conducting in-person motor exams, the systems and techniques described herein enable a patient to conduct virtual clinical exams without clinician supervision. Not only do these techniques enable unsupervised virtual clinical exams, but they also determine when to prompt the patient to perform the virtual clinical exams, including which parts of the virtual clinical exam, the order of the parts, and other such details. To make such determinations, an adaptable triggering mechanism is described that uses a variety of conditions to determine an appropriate real-world scenario in which to present a request relating to a virtual clinical exam. The triggering mechanism is implemented in an exam engine that executes on a user device or a remote server and/or is distributed between the two. Example conditions include a timing condition (e.g., when to administer the virtual clinical exam in terms of an absolute schedule, cyclical duration, event-based timing trigger, or any combination), wearer selection condition (e.g., to whom to administer the virtual clinical exam), environment condition (e.g., where to administer the virtual clinical exam, including location, at home or not, walking or not, or other activity-driven events, where such activity is determined based on the tracked movement or other sensor data on the wearable device), examination setting condition (e.g., which virtual clinical exam to execute, which specified task to request, and the method of delivering the request associated with the virtual clinical exam), and other suitable conditions.

In a particular example, a patient is provided a wearable device such as a watch as part of a program to monitor disease progression. The watch may include a set of sensors configured to track various movements, heart rate, etc. of the patient and software to conduct various virtual clinical exams. The virtual clinical exams may be accessed on demand by the user and/or the watch may suggest a suitable time for conducting an exam. The watch periodically communicates with a server to share data and updates. For example, the watch may receive a set of triggering conditions from the server. The triggering conditions may be associated with a particular virtual clinical exam and/or a task of the particular virtual clinical exam and may be useable by the watch to determine a suitable time for prompting the user to conduct the exam and/or task. A suitable time is one that has a high likelihood of collecting suitable data in a real-world environment, rather than in a controlled clinical environment. In this example, suitable data may be data that is similar to what would be collected in the controlled clinical environment. As the watch collects sensor data from the set of sensors and other non-sensor data, the watch may compare the data to the triggering conditions to determine whether the data fulfills any of the conditions. The relevant data and triggering conditions may depend on the exam and/or the task. When a suitable number of conditions has been fulfilled, the watch may notify the patient by a haptic, sound, etc. and may also update a graphical user interface to present an option to conduct the exam. If the patient selects the option, the watch leads the patient through the exercise and records sensor data during the exercise. This sensor data is then stored, processed, and otherwise sent to the server for additional processing.

This illustrative example is given to introduce the reader to the general subject matter discussed herein, and the disclosure is not limited to this example. The following sections describe various additional non-limiting examples of techniques relating to triggering virtual clinical exams.

The techniques described herein enable one or more technical improvements to the computers that implement virtual clinical exams. For example, battery power of portable user devices may be conserved because sensor sampling rates may be adjusted based on triggered conditions so that lower (more conservative) sampling rates are used when an exam is not being conducted and higher sampling rates are used during the short time period when the exam is being conducted. Additionally, in some examples, the approaches described herein may utilize a consolidated server system to compute triggering conditions for multiple user devices, rather than the user devices computing their own triggering conditions. This approach conserves computing resources on the user devices, which allows these resources to be used for other purposes such as processing sensor data, updated user interfaces, and the like. In other examples, the computation of triggering conditions may be distributed among user devices, with each device computing its own triggering conditions based on historical data that is specific to a user of the user device.

Turning now to the figures, FIG. 1 illustrates a system 102 and a corresponding flowchart illustrating a process 100 for triggering a virtual clinical exam, according to at least one example. The system 102 includes a service provider 104 and a user device 106. FIG. 1 illustrates certain operations taken by the service provider 104 and the user device 106 as it relates to information sharing and exam triggering.

As described in further detail herein, the service provider 104 may be any suitable computing device (e.g., personal computer, handheld device, server computer, server cluster, virtual computer) configured to execute computer-executable instructions to perform operations such as those described herein. The computing devices may be remote from the user device 106. The user device 106, as described herein, is any suitable electronic device (e.g., wearable, implantable, handheld, or home-based) configured to execute computer-executable instructions to perform operations such as those described herein.

The service provider 104 and the user device 106 may be in network communication via any suitable network such as the Internet, a cellular network, and the like. In some examples, the user device 106 may be intermittently in network communication with the service provider 104. For example, the network communications may be enabled to transfer data, e.g., historical virtual motor data for analysis or triggering conditions to trigger virtual clinical exams. In some examples, the user device 106 is in network communication with the service provider 104 via a secondary device. For example, the user device 106, as illustrated, may be a wearable device such as a watch. In this example, the secondary device may be a smartphone that connects to the wearable device via a first network connection (e.g., Bluetooth) and connects to the service provider 104 via a second network connection (e.g., cellular). In some examples, however, the user device 106 may include suitable components to enable the user device 106 to communicate directly with the service provider 104.

The process 100 illustrated in FIG. 1 provides an overview of how the system 102 may be employed to trigger a virtual clinical exam. The process 100 may begin at block 108 by the service provider 104 generating triggering conditions for a virtual clinical exam based on historical data of virtual clinical exams (VCE) 110. The historical data of virtual clinical exams 110 may have been collected by the service provider 104 from a plurality of other user devices 106(a)-106(N). The historical data of virtual clinical exams 110 may include sensor data and non-sensor data that were collected prior to, during, and/or after virtual clinical exams were conducted by the user devices 106(a)-106(N). The historical data may also include other data describing conditions present when prior virtual clinical exams were conducted (e.g., geolocation, weather, clinical data from electronic medical record, etc.). This may include user-input information, device-recorded information, and/or device accessed information. This data may be associated with the particular virtual clinical exams and/or tasks that were performed. At block 108, the service provider 104 may use the historical data 110 to develop a set of heuristics and/or a machine-learning model. Using the heuristics and/or machine-learning model, the service provider 104 may generate the triggering conditions. For example, the machine-learning model may output the triggering conditions based on certain input certain parameters, such as a virtual clinical exam or task identifier, demographics information, disease identifier, disease progression identifier, and the like. In some examples, the user devices 106(a)-106(N), rather than the service provider 104, may generate the triggering conditions. A virtual clinical exam, as described herein, may include a virtual exam for the purposes of assessing motor function, a virtual exam for the purposes of assessing motor function and any other function (e.g., cognitive status), a virtual exam for the purposes of assessing any function and/or system of a human subject (e.g., motor function, cognitive function, circulatory system, digestive system, endocrine system, exocrine system, immune system, muscular system, nervous system, renal system, reproductive system, respiratory system, skeletal system, and any other suitable function or system of a human subject), and a virtual exam for any other purposes.

Once the triggering conditions have been generated by the service provider 104, at block 112, the user device 106 may receive the triggering conditions from the service provider 104. The user device 106 may store the triggering conditions in memory on the user device 106. In some examples, when the user device 106 generates the triggering conditions, block 112 may include accessing the triggering conditions from memory of the user device 106.

At block 114, the user device 106 collects sensor data, which is sometimes referred to herein as dynamic data or dynamic sensor data. This may include collecting sensor data while not conducting a virtual clinical exam. The user device 106 may reference non-sensor data, such as demographic data, calendar data, location data, electronic medical record (EMR) data, time of day data, or any other suitable type of non-sensor data, which is sometimes referred to herein as static data.

At block 116, the user device 106 determines fulfillment of at least one triggering condition using the sensor data. In some examples, this may include the user device 106 comparing the incoming sensor data and, in some examples, non-sensor data to the triggering conditions.

At block 118, the user device 106 presents the virtual clinical exam. In some examples, this may include presenting the virtual clinical exam that was triggered by fulfillment of one or more triggering conditions. Presenting the virtual clinical exam may include notifying the user, receiving an indication of intent to proceed from the user (e.g., selection of user interface element prompt), and instructing the user in one or more tasks associated with the virtual clinical exam.

At block 120, the user device 106 collects additional data during the virtual clinical exam. The additional data may be indicative of how the user performed portions of the virtual clinical exam. For example, if a task of the exam required the user to sit and stand, the additional data may be sensor data and may indicate a speed and smoothness at which the user was able to sit and stand. In some examples, the additional data may include user-input information such as a self-report of how the user felt during the task.

At block 122, the user device 106 outputs results of the virtual clinical exam based on the additional data. For example, the additional data can be compared to baseline data for the user, data of other users, and/or an exam standard to determine disease progression. This information may be shared with the service provider 104 and/or presented to the user of the user device 106 (e.g., via a graphical user interface).

Figure 2:
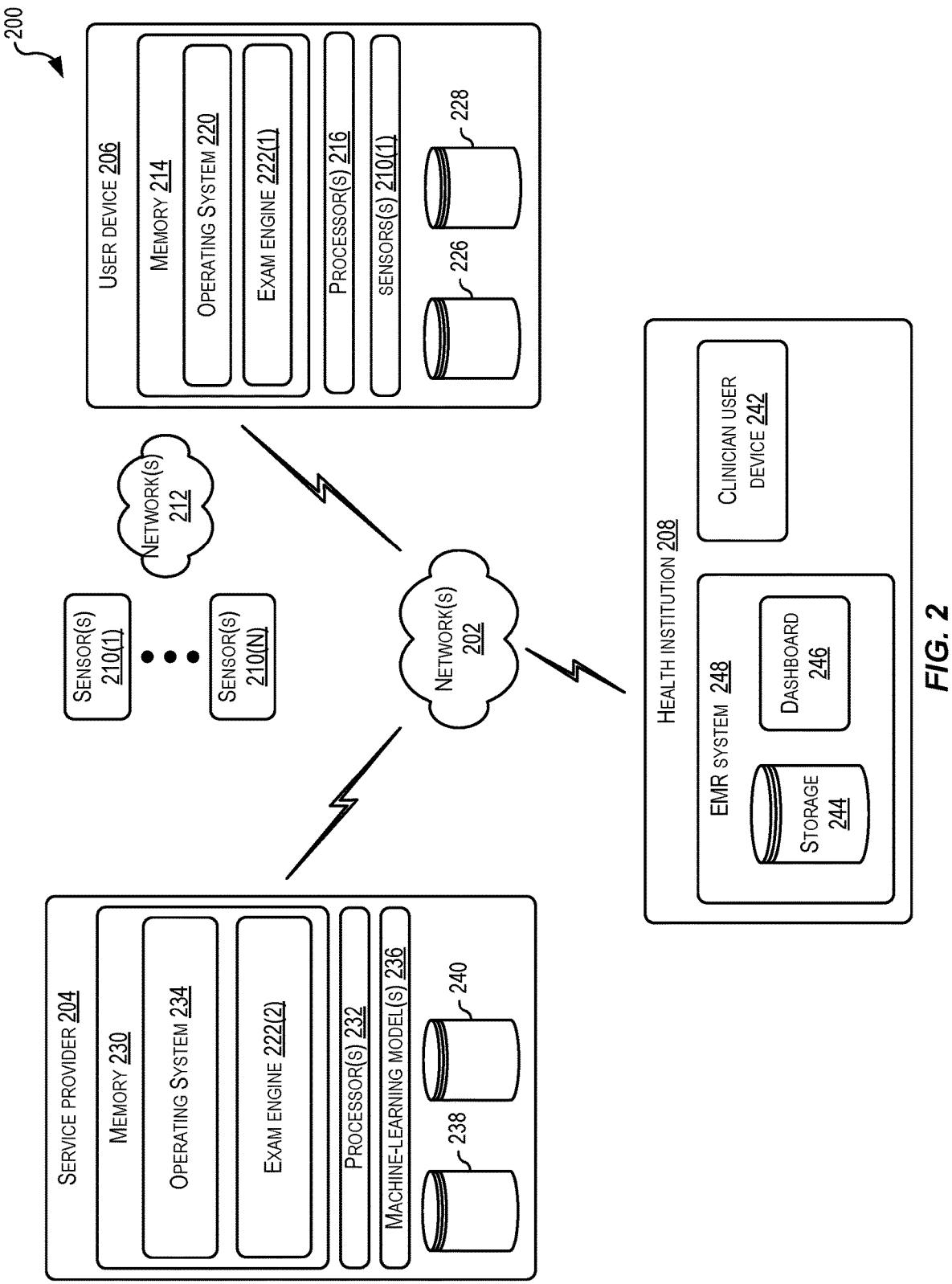
FIG. 2 illustrates an example architecture for implementing techniques relating to triggering virtual clinical exams, according to at least one example.

FIG. 2 illustrates an example architecture or environment 200 configured to implement techniques relating to triggering virtual clinical exams, according to at least one example. For example, the architecture 200 enables data sharing between the various entities of the architecture, at least some of which may be connected via one or more networks 202, 212. For example, the example architecture 200 may be configured to enable a user device 206 (e.g., the user device 106), a service provider 204 (e.g., the service provider 104, sometimes referred to herein as a remote server, service-provider computer, and the like), a health institution 208, and any other sensors 210 to share information. In some examples, the service provider 204, the user device 206, the health institution 208, and the sensors 210(1)-210(N) may be connected via one or more networks 202 and/or 212 (e.g., via Bluetooth, WiFi, the Internet, cellular, or the like). In the architecture 200, one or more users may utilize a different user device to manage, control, or otherwise utilize the user device 106, via the one or more networks 212 (or other networks). Additionally, in some examples, the user device 106, the service provider 204, and the sensors 210 may be configured or otherwise built as a single device such that the functions described with respect to the service provider 204 may be performed by the user device 206 and vice versa.

In some examples, the networks 202, 212 may include any one or a combination of many different types of networks, such as cable networks, the Internet, wireless networks, cellular networks, satellite networks, other private and/or public networks, or any combination thereof. While the illustrated example represents the user device 206 accessing the service provider 204 via the networks 202, the described techniques may equally apply in instances where the user device 206 interacts with the service provider 204 over a landline phone, via a kiosk, or in any other manner. It is also noted that the described techniques may apply in other client/server arrangements (e.g., set-top boxes), as well as in non-client/server arrangements (e.g., locally stored applications, peer-to-peer configurations).

As noted above, the user device 206 may be configured to collect and/or manage user activity data potentially received from the sensors 210. In some examples, the user device 206 may be configured to provide health, fitness, activity, and/or medical data of the user to a third- or first-party application (e.g., the service provider 204). In turn, this data may be used by the service provider 204 in implementing techniques described herein.

The user device 206 may be any type of computing device, such as, but not limited to, a mobile phone, a smartphone, a personal digital assistant (PDA), a wearable device (e.g., ring, watch, necklace, sticker, belt, shoe, shoe attachment, belt-clipped device) an implantable device, or the like. In some examples, the user device 206 may be in communication with the service provider 204; the sensors 210; and/or the health institution via the networks 202, 212; or via other network connections.

The sensors 210 may be standalone sensors or may be incorporated into one or more devices. In some examples, the sensors 210 may collect sensor data that are shared with the user device 206 and related to implementing the techniques described herein. For example, the user device 206 may be a primary user device 206 (e.g., a smartphone) and the sensors 210 may be sensor devices that are external from the user device 206 and can share sensor data with the user device 206. For example, external sensors 210 may share information with the user device 206 via the network 212 (e.g., via Bluetooth or other near-field communication protocol). In some examples, the external sensors 210 include network radios that allow them to communicate with the user device 206 and/or the service provider 204. The user device 206 may include one or more applications for managing the remote sensors 210. This may enable pairing with the sensors 210, data reporting frequencies, data processing of the data from the sensors 210, data alignment, and the like.

The sensors 210 may be attached to various parts of a human body (e.g., feet, legs, torso, arms, hands, neck, head, eyes) to collect various types of information, such as activity data, movement data, or heart rate data. The sensors 210 may include accelerometers, respiration sensors, gyroscopes, photoplethysmography (PPG) sensors, pulse oximeters, electrocardiogram (ECG) sensors, electromyography (EMG) sensors, electroencephalography (EEG) sensors, global positioning system (GPS) sensors, auditory sensors (e.g., microphones), ambient light sensors, barometric altimeters, electrical and optical heart rate sensors, and any other suitable sensor designed to obtain physiological data, physical condition data, and/or movement data of a patient.

In one illustrative configuration, the user device 206 may include at least one memory 214 and one or more processing units (or processor(s)) 216. The processor(s) 216 may be implemented as appropriate in hardware, computer-executable instructions, firmware, or combinations thereof. Computer-executable instruction or firmware implementations of the processor(s) 216 may include computer-executable or machine-executable instructions written in any suitable programming language to perform the various functions described. The user device 206 may also include geo-location devices (e.g., a GPS device or the like) for providing and/or recording geographic location information associated with the user device 206. The user device 206 also includes one or more sensors 210(2), which may be of the same type as those described with respect to the sensors 210.

Depending on the configuration and type of the user device 206, the memory 214 may be volatile (such as random-access memory (RAM)) and/or non-volatile (such as read-only memory (ROM), flash memory). While the volatile memory described herein may be referred to as RAM, any volatile memory that would not maintain data stored therein once unplugged from a host and/or power would be appropriate.

Both the removable and non-removable memory 214 are examples of non-transitory computer-readable storage media. For example, non-transitory computer-readable storage media may include volatile or non-volatile, removable or non-removable media implemented in any method or technology for storage of information such as computer-readable instructions, data structures, program modules, or other data. The memory 214 is an example a of non-transitory computer-readable storage media or non-transitory computer-readable storage device. Additional types of computer storage media that may be present in the user device 206 may include, but are not limited to, phase-change RAM (PRAM), static random-access memory (SRAM), dynamic random-access memory (DRAM), RAM, ROM, electrically erasable programmable read-only memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 206. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

Figure 3:
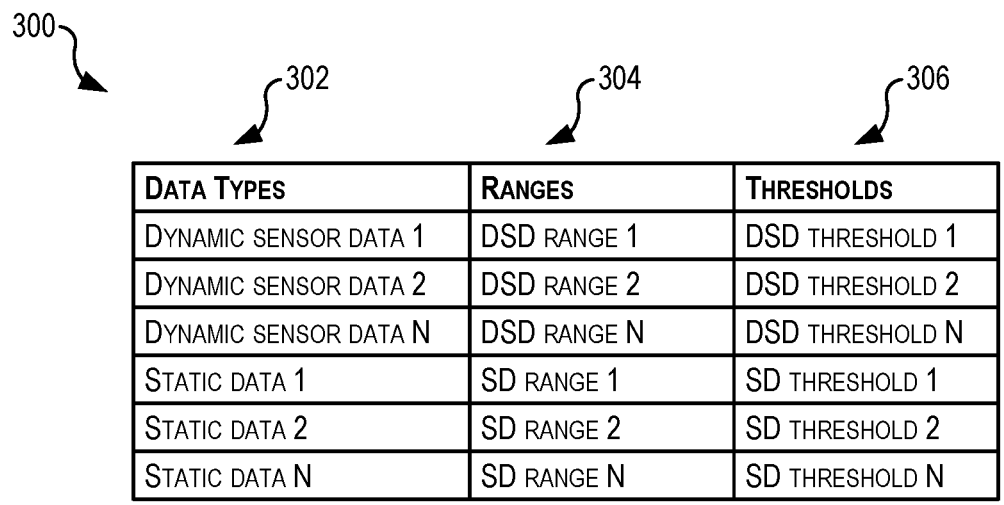
FIG. 3 illustrates a data table relating to triggering presentation of virtual clinical exams, according to at least one example.

Turning to the contents of the memory 214 in more detail, the memory 214 may include an operating system 220 and/or one or more application programs or services for implementing the features disclosed herein including an exam engine 222(1). In some examples, the exam engine 222 may be configured to implement the features described herein. For example, as introduced in FIG. 1 and described in more detail with respect to FIG. 6, the exam engine 222(1) executing in the user device 206 may receive triggering information from the service provider 204, collect different types of sensor data such as dynamic sensor data (e.g., data collected from sensors) and static sensor data (e.g., data obtained from a static record such as demographic or electronic medical record data), and use the triggering information and sensor data to determine when to present a virtual clinical exam. Examples of triggering information are shown in FIG. 3.

The service provider 204 may also include a memory 224 that includes an exam engine 222(2). In this manner, the techniques described herein may be implemented by any one, or a combination of more than one, of the computing devices (e.g., the user device 206 and the service provider 204).

The user device 206 also includes a datastore that includes one or more databases or the like for storing data such as sensor data 226 and static data 228. In some examples, the databases 226 and 228 may be accessed via a network service.

The service provider 204 may also be any type of computing device, such as, but not limited to, a mobile phone, a smartphone, a PDA, a laptop computer, a desktop computer, a thin-client device, a tablet computer, a wearable device, a server computer, or a virtual machine instance. In some examples, the service provider 204 may be in communication with the user device 206 and the health institution 208 via the network 202 or via other network connections.

In one illustrative configuration, the service provider 204 may include at least one memory 230 and one or more processing units (or processor(s)) 232. The processor(s) 232 may be implemented as appropriate in hardware, computer-executable instructions, firmware, or combinations thereof. Computer-executable instruction or firmware implementations of the processor(s) 232 may include computer-executable or machine-executable instructions written in any suitable programming language to perform the various functions described.

The memory 230 may store program instructions that are loadable and executable on the processor(s) 232, as well as data generated during the execution of these programs. Depending on the configuration and type of service provider 204, the memory 230 may be volatile (such as RAM) and/or non-volatile (such as ROM, flash memory). While the volatile memory described herein may be referred to as RAM, any volatile memory that would not maintain data stored therein once unplugged from a host and/or power would be appropriate. Both the removable and non-removable memory 230 are additional examples of non-transitory computer-readable storage media.

Turning to the contents of the memory 230 in more detail, the memory 230 may include an operating system 234 and/or one or more application programs or services for implementing the features disclosed herein including the exam engine 222(2). For example, as introduced in FIG. 1 and described in further detail in FIG. 5, the exam engine 222(2) executing in the service provider 204 may collect historical virtual clinical exam data from user device 206, process this historical data to determine a set of triggering conditions (e.g., some of the data in data table 300), and share the set of triggering conditions with a particular user device 206. The service provider 204 also includes one or more machine-learning models 236 representing any suitable predictive model. The machine-learning models 236 may be utilized by the service provider 204 to determine the set of triggering conditions (e.g., some of the data in the data table 300) described herein. In some examples, the machine-learning models 236 may be used to determine triggering conditions, as described herein. The machine-learning models 236 may be managed using tools provided by the exam engine 222(2).

The service provider 204 also includes a datastore that includes one or more databases or the like for storing data, such as sensor data 238 and static data 240. In some examples, the databases 238 and 240 may be accessed via a network service.

Turning now to the health institution 208, the health institution 208, while depicted as a single entity, may represent multiple health institutions. The health institution 208 includes an EMR system 248, which is accessed via a dashboard 246 (e.g., by a user using a clinician user device 242). In some examples, the EMR system 248 may include a record storage 244 and a dashboard 246. The record storage 244 may be used to store health records of patients associated with the health institution 208. The dashboard 246 may be used to read and write the records in the record storage 244. In some examples, the dashboard 246 is used by a clinician to manage disease progression for a patient population including a patient who operates the user device 106. The clinician may operate the clinician user device 242 to interact with the dashboard 246 to view results of virtual clinical exams on a patient-by-patient basis, on a population of patient basis, etc. In some examples, the clinician may use the dashboard 246 to "push" an exam to the user device 106.

FIG. 3 illustrates a data table 300 relating to triggering presentation of virtual clinical exams, according to at least one example. The data in the data table 300 may be representative of data used to generate a set of triggering conditions, as described herein. In some examples, the entries in the data table 300 may themselves be triggering conditions.

Turning to the details of the data table 300, the data table 300 may include a set of data types 302, a set of ranges 304 for the data types 302, and a set of thresholds 306 for the data types 302. The set of data types 302 may include different types of dynamic sensor data (e.g., dynamic sensor data 1, dynamic sensor data 2, and dynamic sensor data N) and different types of static data (e.g., static data 1, static data 2, and static data N). The dynamic sensor data are data that are generated by sensors of the user device 206 and/or from external sensors 210(1)-2010(N). For example, the dynamic sensor data 1 may be data from an accelerometer, the dynamic sensor data 2 may be data from a gyrometer, and the dynamic sensor data N may represent any other type of data obtained from a sensor of the user device 106, an external sensor 210, and/or in any other dynamic manner (e.g., data relating to weather conditions, perspiration, heart rate, stress levels, glycemic levels, breathing rates, location data).

The static data are data that are obtained from other sources outside the user device 106 and/or stored on the user device 106 and which have a lower likelihood of changing or at least change less frequently than the dynamic sensor data. For example, the static data may include demographic data, calendar data (e.g., indicating free and unavailable time periods), electronic medical record (EMR) data, and the like. The ranges 304 may define a set of ranges for the data types 302, each of which may be specific to a particular triggering condition and/or exam. For example, a threshold triggering condition for most tasks may be that the user is awake. Thus, a dynamic sensor data type 302 (e.g., accelerometer data) may include a range of values 304 indicative of being awake. A threshold 306 for this range 304 may require that the user have values within the range (or outside of the range, depending on the definition of the range) for some period of time or values that fall below or above the range at some magnitude. The data types 302, the ranges 304, and the thresholds 306 are all independently configurable to define different conditions, depending on the task and/or exam to be conducted.

Figure 4:
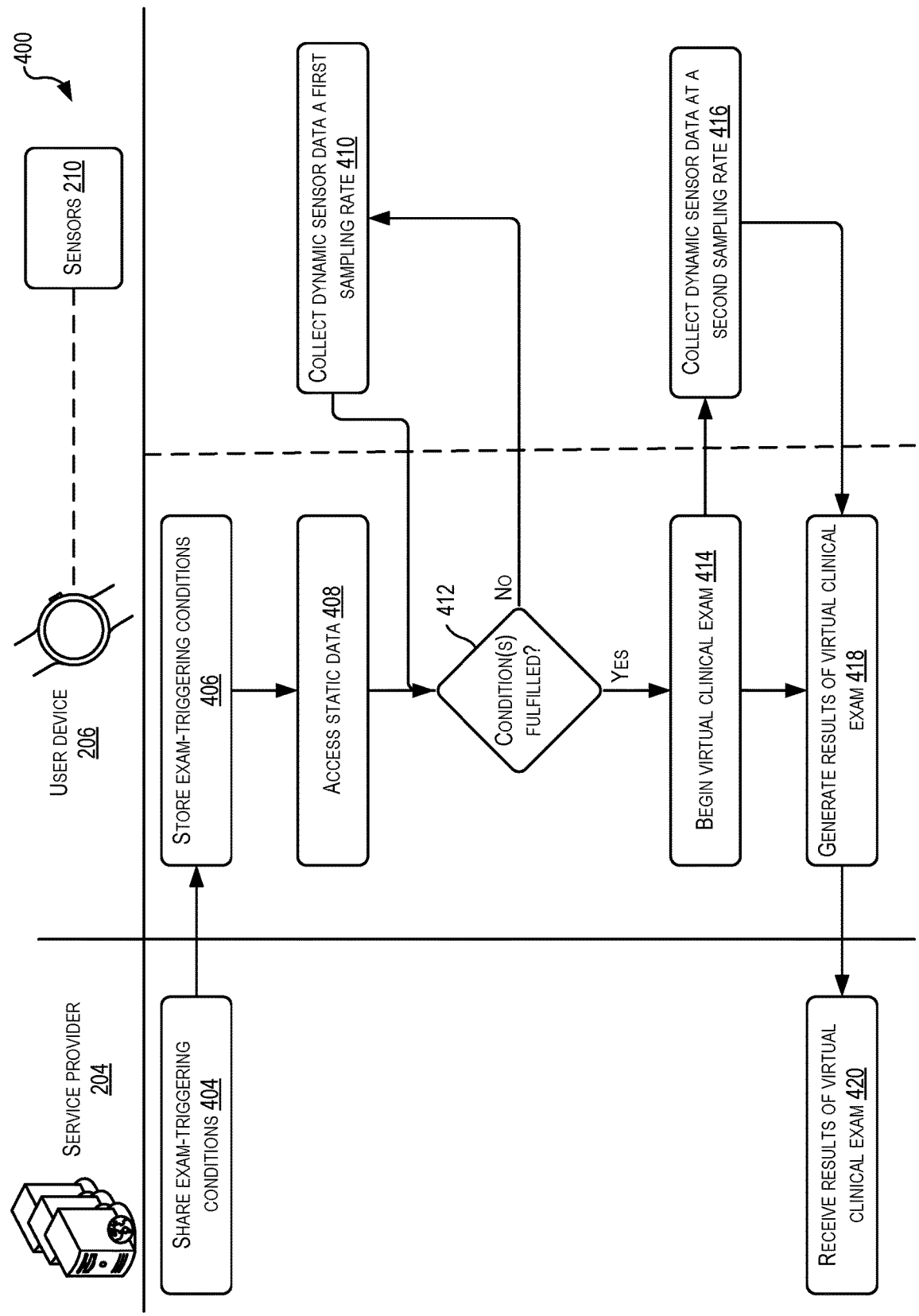
FIG. 4 illustrates an example flowchart illustrating a process relating to implementing techniques relating to triggering virtual clinical exams, according to at least one example.
Figure 5:
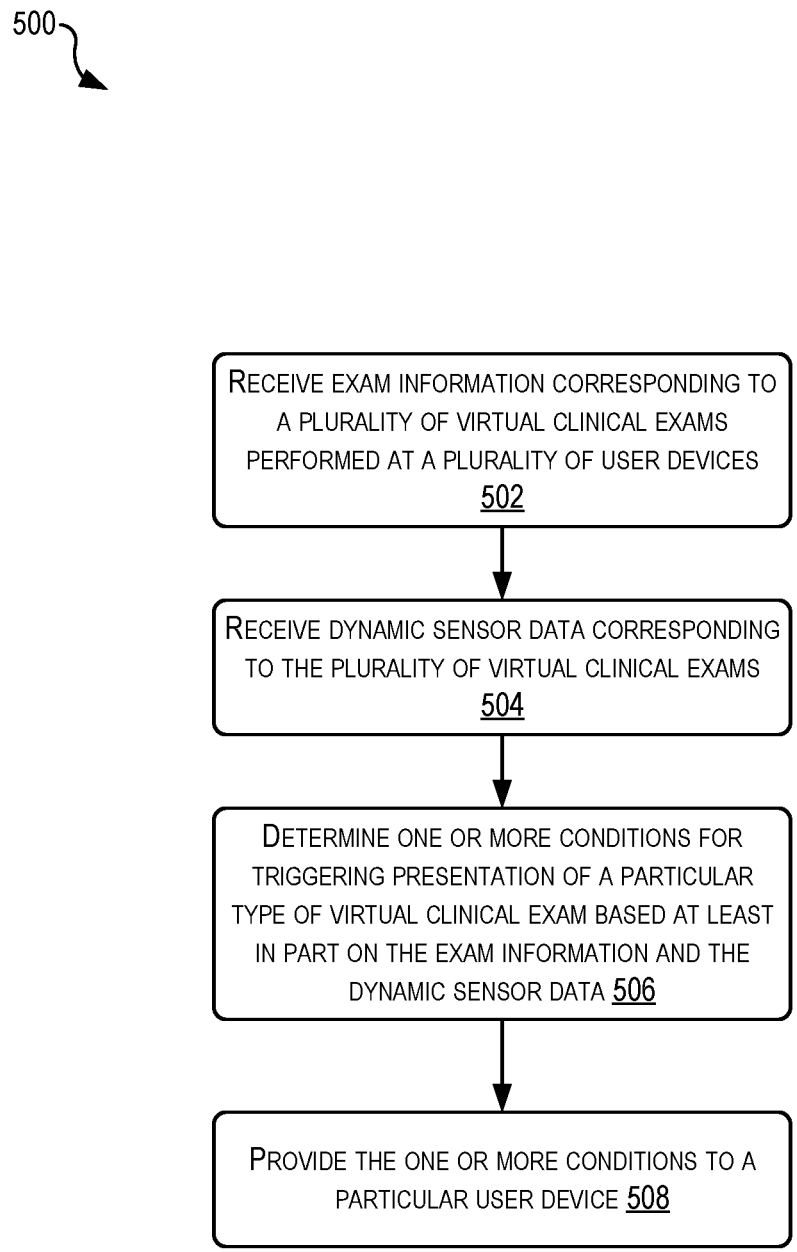
FIG. 5 illustrates an example flowchart illustrating a process relating to implementing techniques relating to triggering virtual clinical exams, according to at least one example.
Figure 6:
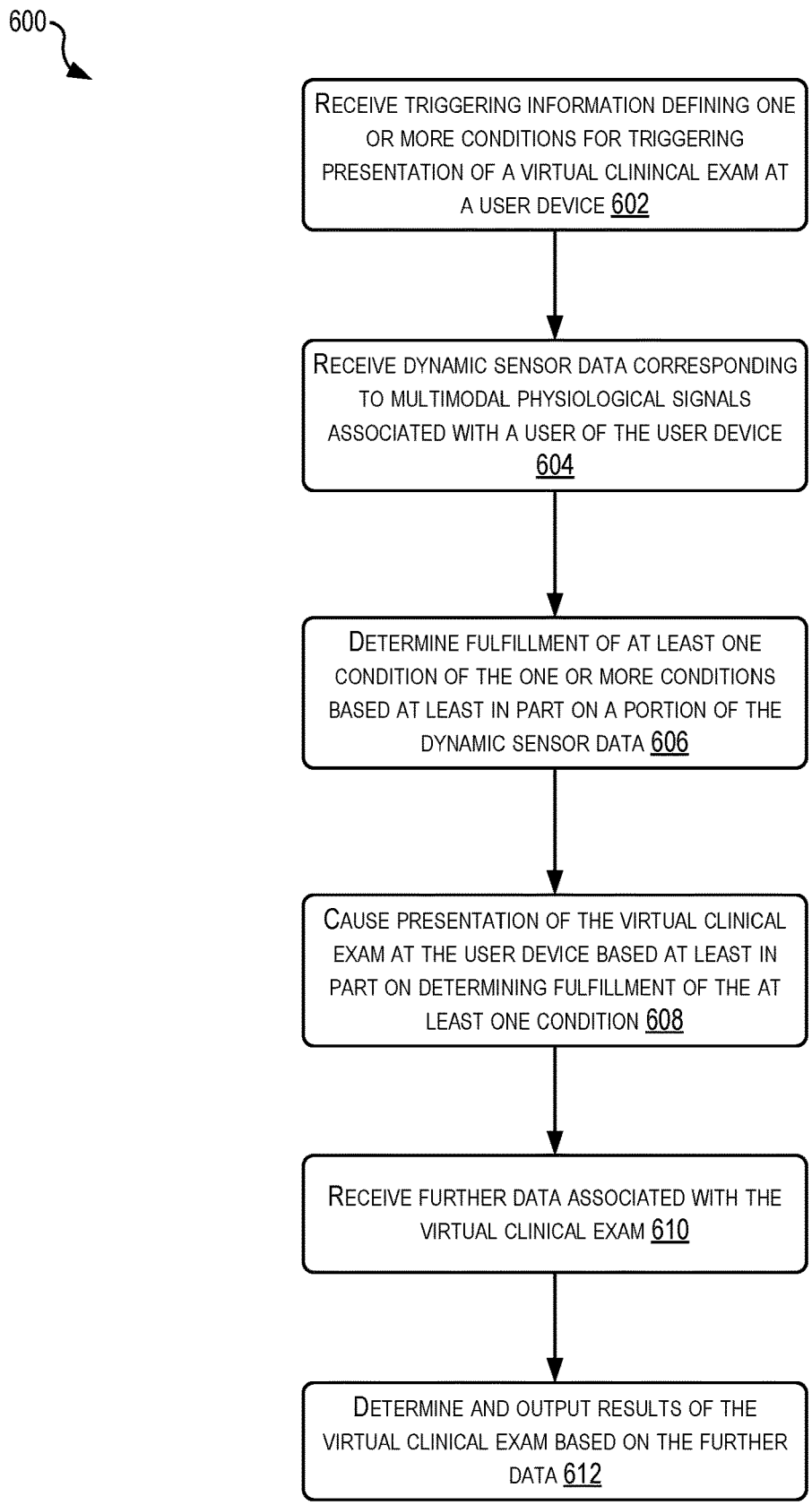
FIG. 6 illustrates an example flowchart illustrating a process relating to implementing techniques relating to triggering virtual clinical exams, according to at least one example.

FIGS. 4-6 illustrate example flow diagrams showing processes 400, 500, and 600, according to at least a few examples. These processes, and any other processes described herein (e.g., the process 100), are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

FIG. 4 illustrates an example flowchart illustrating the process 400 relating to implementing techniques relating to triggering virtual clinical exams, according to at least one example. The process 400 in this example is performed by the service provider 204 (FIG. 2), the user device 206 (FIG. 2), and sensors 210 (FIG. 2) of the user device 206; however any suitable system or device according to this disclosure may be employed. The process 400 in particular corresponds to collecting sensor data at a variety of sampling rates depending on whether a virtual exam is being conducted.

The process 400 begins at block 404 by the service provider 104 sharing exam-triggering conditions to the user device 206. The exam-triggering conditions may have been generated by the service provider 204, as described with reference to FIG. 5. At block 406, the user device 206 stores the exam-triggering conditions. This may include storing the exam-triggering conditions in memory of the user device 206. At block 408, the user device 106 accesses static data. This may include the user device 206 accessing static data from memory of the user device 206 and/or receiving from a different user or computing device. At block 410, the sensors 210 collect dynamic sensor data at a first sampling rate. The user device 206 may instruct the sensors 210 to collect the dynamic sensor data. The sensors 210 may collect the dynamic sensor data at the first sampling rate when the user device 206 is turned on and being worn by the user.

The sensor data collected at the first sampling rate may be used by the user device 206 at block 412 to determine whether one or more of the exam-triggering conditions have been fulfilled. The user device 206 may continuously evaluate exam-triggering conditions for multiple exams simultaneously. To conserve computing resources and battery life, the user device 206 may determine a subset of all possible exams for which to evaluate. For example, an exam may include multiple tasks that need to be performed within some fixed period (e.g., six hours), so the user device 106 may attempt to find a single block of time suitable for performing all tasks, which may require multiple fulfilment of multiple triggering conditions. In some examples, the user device 206 may attempt to find multiple blocks of time suitable for performing all tasks, which may include finding a first time suitable for performing a first task, a second time suitable for performing a second task, etc. until all tasks have been performed. The virtual clinical exams defined herein may be triggered without user input (e.g., without the user using the user device 206 to request an exam). In some examples, however, the user may request the user device 206 to perform a virtual clinical exam. In some examples, the user device 206 may use a user input as a trigger for determining an appropriate time for performing an exam. For example, a user may request to perform an exam, after which, the user device 206 may evaluate the triggering conditions associated with the exam to determine whether the exam should actually be performed. For example, even though the user has requested the exam, the timing may not be appropriate (e.g., the user's heart rate may be too high, she may be traveling in a vehicle, etc.). In this example, the user device 206 may provide feedback in the form of a notification to the user as to why the exam will not be performed (e.g., "It looks like your heart rate is too high to perform this exam. Try sitting down and taking a few deep breaths before trying again."). In some examples, the user device 206 may include functionality to enable the user to override the user device's 206 decision to not present the exam, even if exam triggering conditions associated with the particular exam have not been fulfilled.

As described with respect to FIG. 3, determining whether a condition is fulfilled may include evaluating whether the data collected and accessed at 410 and 408 fulfills any of the exam-triggering conditions. For example, for a motor exam that tests standing up and sitting down from a chair, a first condition may require that the user has mobility (e.g., is not confined to a wheelchair), as defined by a value in the static data accessed at 408. A second condition may require that the user's heart rate is within some "normal" range (e.g., between 40 and 80 beats per minute, below 90 beats per minute, etc.) for some fixed period of time (e.g., five minutes), as obtained from a heart rate sensor of the user device 206 as dynamic sensor data collected at 410. A third condition may require that the user is not showing signs of stress, as obtained from a heart rate sensor, a skin wetness sensor, etc. of the user device 206 as dynamic sensor data collected at 410. If the triggering conditions for this exam require fulfillment of all three conditions, then, when these three conditions have been fulfilled, the user device 206 may progress to 414.

In some examples, the static data 408 may also be used by the user device 206 at block 412. If the answer at 412 is "NO" (at least one condition or a subset of the conditions are not fulfilled), the sensors 210 may continue to collect dynamic sensor data at the first sampling rate. If the answer at 412 is "YES" (the conditions are fulfilled), the user device 206 may, at block 414, begin a virtual clinical exam. This may be the virtual clinical exam that is associated with the exam-triggering conditions stored at block 406. When the virtual clinical exam begins at 414, the user device 206 may command the sensors 210 to begin, at block 416, collecting sensor data at a second sampling rate. In some examples, all sensors of the user device 206 collect sensor data at the second sampling rate. In some examples, only a subset of the sensors 210 collect data at the second sampling rate. Which sensors 210 are included in the subset of the sensors 210 may be determined by the user device 206 (e.g., by accessing a reference table that associates exams and sensors or at least exam tasks and sensors) or may be provided to the user device 206 together with the exam-triggering conditions at 404 and/or derived from the exam-triggering conditions. In any event, at least some sensors 210 may collect sensor data at the second sampling rate while the virtual clinical exam is being conducted at block 414. The first and second sampling rates may be different. For example, the second sampling rate may be higher than the first sampling rate. This may enable the user device 206 to collect more granular data during the exam. In some examples, the user device 206 may operate in multiple different modes, such as an exam mode and non-exam mode. The non-exam mode may correspond to the first sampling rate and the exam mode may correspond to the second sampling rate. At block 418, the user device 206 generates results of the virtual clinical exam. These results may include how the user performed on the exam (e.g., a computed score), the underlying sensor and/or input data used to compute the score, tags for the sensor data, the sensor data, and any other information generated by the user device 206 as part of conducting the exam. At block 420, the service provider 204 may receive results of the virtual clinical exam from the user device 106. These may be shared on demand, periodically, when prompted, and/or in any suitable manner. In some examples, block 418 may be performed by the service provider 204. For example, after the virtual clinical exam has concluded and/or during execution of the exam, the user device 206 may send the data about the exam to the service provider 204, and the service provider 204 may generate the results. In some examples, the service provider 204 may share those results with the user device 206.

FIG. 5 illustrates an example flowchart illustrating the process 500 relating to implementing techniques relating to triggering virtual clinical exams, according to at least one example. The process 500 is performed by the service provider 204 (FIG. 2) (e.g., the exam engine 222(2) and the machine-learning model 236). The process 500 in particular corresponds to collecting exam information from a variety of user devices that have conducted virtual clinical exams, and using that information to determine triggering conditions for a particular user of a particular user device.

The process 500 begins at block 502 by the service provider 204 receiving exam information corresponding to a plurality of virtual clinical exams performed by a plurality of user devices. The exam information may be received from a plurality of user devices. The exam information may identify at least a virtual clinical exam type for each of the plurality of virtual clinical exams. In some examples, the exam information may identify at least beginning times and ending times for the plurality of virtual clinical exams. In some examples, the plurality of virtual clinical exams is tailored to one or more movement disorders. For example, the plurality of virtual clinical exams may be based at least in part on the unified UPDRS, Modified Hoen and Yahr Scale, Schwab and England Activities of Daily Living Scale, Abnormal Involuntary Movement Scale, and any other virtual clinical exam suitable for diagnosing, preventing, or tracking progress of ataxia, cervical dystonia, chorea, dystonia, functional movement disorder, Huntington's disease, multiple system atrophy, myoclonus, Parkinson's disease, Parkinsonism, progressive supranuclear palsy, restless leg syndrome, Tardive dyskinesia, Tourette syndrome, tremors, Wilson's disease, and any others.

At block 504, the process 500 includes the service provider 204 receiving dynamic sensor data corresponding to the plurality of virtual clinical exams. The dynamic sensor data may be received from the plurality of user devices. The dynamic sensor data may have been collected by one or more sensors of the plurality of user devices. The dynamic sensor data may include raw sensor data collected by one or more sensors, such as those described with respect to sensors 210. For each virtual clinical exam, corresponding the dynamic sensor data may be tagged to define a beginning and an end of the respective virtual clinical exam. In addition, for each virtual clinical exam, the corresponding dynamic sensor data may include data covering a time period prior to the beginning tag. This "prior" dynamic sensor data may represent the actual conditions prior to the exam being conducted (e.g., the sensor readouts before the user requested the exam or the exam was otherwise requested).

At block 506, the process 500 includes the service provider 204 determining one or more conditions for triggering presentation of a particular type of virtual clinical exam based at least in part on the exam information and the dynamic sensor data. For example, to determine the one or more conditions for triggering the particular type of virtual moto exam, the service provider may evaluate the "prior" dynamic sensor data for many occurrences of the particular type of virtual clinical exam to identify patterns in the data (e.g., readouts from sensor 1 are typically within range A-B, readouts of sensor 2 are typically below value C, readouts from sensor 3 are typically above value D, etc.). These patterns may then be turned into triggering conditions such as defined in data table 300.

In some examples, determining the one or more conditions may include include training a machine-learning model using the exam information and the dynamic sensor data as inputs to the machine-learning model, and obtaining the conditions from the machine-learning model. In some examples, the determining at block 506 may be performed using the machine-learning model. The model may be configured to identify the value ranges of certain sensor data before, during, and after virtual clinical exams have been performed. This information may be used to generate a data table such as the data table 200 described herein. In some examples, instead of or in addition to the machine-learning model, the one or more conditions may be determined heuristically. For example, a human user may, with the assistance of computer software, determine the value ranges for certain sensors, thresholds, and/or any other information that may be helpful for a computer system such as the user device 106 to determine an appropriate time for conducting a virtual exam. In some examples, the one or more conditions define one or more value ranges for the dynamic sensor data.

At block 508, the process 500 includes the service provider 204 providing the one or more conditions to a particular user device. The particular user device may use the one or more conditions as part of triggering presentation of the particular type of virtual clinical exam at the particular user device.

In some examples, the process 500 may further include receiving updated exam information associated with presentation of the particular type of virtual clinical exam at the particular user device, receiving updated dynamic sensor data associated with presentation of the particular type of virtual clinical exam at the particular user device, or updating the one or more conditions based at least in part on the updated exam information and the updated dynamic sensor data. In this manner, the information collected by the particular user device may be used to update future presentations of the virtual clinical exam at the particular user device and/or at other user devices.

In some examples, the process 500 may further include receiving static data including at least health record data or demographic data. In some examples, the block 506 of determining the one or more conditions may include determining the one or more conditions based at least in part on the static data.

In some examples, the process 500 may further include receiving user profile information corresponding to a particular user profile that is associated with the particular user device. In some examples, the block 506 of determining the one or more conditions may include determining the one or more conditions based at least in part on the user profile information.

FIG. 6 illustrates an example flowchart illustrating the process 600 relating to implementing techniques relating to triggering virtual clinical exams, according to at least one example. The process 600 is performed by the user device 206 (FIG. 2) (e.g., the exam engine 222(1)). The process 600 in particular corresponds to determining fulfillment of triggering conditions and presenting a virtual clinical exam based on the same.

The process 600 begins at block 602 by the user device 206 receiving triggering information defining one or more conditions for triggering presentation of a virtual clinical exam at the user device. In some examples, the triggering information may be received from a remote computing device (e.g., the service provider 204). For example, the service provider 204 may perform the process 500 to generate the triggering information, which is then shared with the user device 206 and used by the user device 206 to perform the remaining blocks of the process 600. In some examples, the triggering information may be based at least in part on historical scenarios in which the virtual clinical exam was presented to other user devices associated with other users. The virtual clinical exam may be configured to test at least one motor skill relating to a movement disorder, as described herein. In some examples, the virtual clinical exam may test for disease progression of the movement disorder. In some examples, the one or more conditions may include a plurality of value ranges including at least one value range for the dynamic sensor data and at least one value range for static data, and the static data may include at least one of demographic data or health record data. The conditions may be specific to a user of the user device. The user device may be a wearable user device, such as a watch.

At block 604, the process 600 includes the user device 206 receiving dynamic sensor data corresponding to multimodal physiological signals associated with a user of the user device. The dynamic sensor data may be collected by and received from one or more sensors, which may be part of the user device and/or may be separate and distinct from the user device, as described herein.

At block 606, the process 600 includes the user device 206 determining fulfillment of at least one condition of the one or more conditions based at least in part on a portion of the dynamic sensor data. In some examples, at least two conditions may be met, or at least half the conditions, all conditions may be met, or any variation between at least one and all conditions. Determining fulfillment of the condition(s) at the block 606 may be performed as described with respect to the block 412 of FIG. 4. In some examples, the at least one condition may define a value range for the dynamic sensor data, such as illustrated in FIG. 3. In this example, determining fulfillment of the at least one condition at block 606 may include determining that at least one value of the dynamic sensor data is in the value range or outside of the value range. For example, as discussed with reference to the block 412.

At block 608, the process 600 includes the user device 206 causing presentation of the virtual clinical exam at the user device based at least in part on determining fulfillment of the at least one condition. Causing presentation of the virtual clinical exam may include sending a notification to the user device in the form of an alert, haptic buzz, etc. A prompt may also be presented in a graphical user interface of the user device (e.g., a "conduct exam now" button may be placed on the graphical user interface). In some examples, a graphical user interface of the user device 206 may be updated to lead the user through the virtual clinical exam. This may include providing instructions to the user, requesting tagging of a beginning and end of the exam, soliciting feedback from the user, and the like.

While a single condition may be sufficient to cause presentation of the virtual clinical exam, in many cases, more than one condition may be present. For example, for presentation of an exam that tests tremor, it may be important that the user is not sleeping (e.g., a first condition), is not sitting down (e.g., a second condition), has a normal heart rate (e.g., third condition), is not in a meeting as indicated by calendar data that references a user's digital calendar (e.g., fourth condition), is not driving (e.g., fifth condition), and that a suitable amount of time has passed since the last exam (e.g., a sixth condition). The sixth condition may be referred to as a usability condition, which attempts to avoid overburdening a user with exams. This may define that only a certain number of exams should be presented within any given time period, or that a certain amount of time should pass between presenting exams. Thus, in some examples, the systems described herein evaluate multiple conditions to determine the most appropriate time for presenting an exam. The conditions may be specific to the user (e.g., a calendar condition as described above, a usability condition as described above, a demographic condition), may be specific to the exam (e.g., user needs to be standing vs. sitting, user needs normal vs. elevated heart rate), or may be specific to other factors.

At block 610, the process 600 includes the user device 206 receiving further data associated with the virtual clinical exam, which may include activating certain sensors and/or commanding them to send further dynamic sensor data and/or non-sensor data. In some examples, this may include deactivating certain other sensors and/or changing the sampling rates of the sensors, as described with respect to FIG. 4. The further data may be received from the one or more sensors while the user device 206 conducts the virtual clinical exam and/or from other sensors of the user device 206. For example, as described with reference to FIG. 4, the user device 206 may collect further dynamic sensor data while the exam is being conducted. In some examples, the type of sensor data and the corresponding sensors used to at the block 604 are different from the further data received at the block 610. In some examples, the at least some of the sensors are the same. In some examples, the further dynamic sensor data are sampled at a higher sampling rate than the dynamic sensor data collected previously.

At block 612, the process 600 includes determining and outputting results of the virtual clinical exam based on the further data. In some examples, determining the results of the virtual clinical exam may include performing at least some processing of the further dynamic sensor data such as tagging the data to identify a beginning and an and, receiving subjective feedback from the user (e.g., "on a scale of 1-5, pick how well you think you did on this exam"), and otherwise determining whether the user was able to complete the exam. Outputting the results may include sending the results to the service provider 204 or other remote computing device. In some examples, the block 612 may be performed similar to the block 418 of FIG. 4.

In some examples, determining the results may include bundling the data collected while the exam was conducted and, without processing the data, sending the unprocessed data to the service provider 204 or other remote computing device. In some examples, data for a fixed period before and fixed period after the exam was conducted may also be sent to the service provider.

In some examples, outputting the results of the exam may include outputting to a display of the user device 206 completion of the exam, metrics as to how the user performed on the exam, questions for the user to answer about the exam, and any other suitable information about the exam.

In some examples, outputting the results may also include sending the triggering conditions used to trigger the exam together with the bundled data to the service provider 204. This may correspond to the exam information received by the service provider at the block 502 and the dynamic sensor data received at the block 504.

In some examples, the process 600 may further include generating a notification based at least in part on the results of the virtual clinical exam, and sending the notification to a healthcare provider associated with the user. In some examples, the process 600 may further include updating an electronic health record associated with the user based at least in part on the results of the virtual clinical exam, and scheduling an appointment with a healthcare provider based at least in part on the results of the virtual clinical exam.

In some examples, the process 600 may further include determining fulfillment of at least one other condition of the one or more conditions based at least in part on the dynamic sensor data, and determining a likelihood of success of the virtual clinical exam based at least in part on fulfillment of the at least one condition and the at least one other condition. In this example, the block 608 of causing presentation of the virtual clinical exam may include causing presentation of the virtual clinical exam when the likelihood of success exceeds a threshold.

In some examples, the virtual clinical exam may include a plurality of tasks. In this example, the block 608 of causing presentation of the virtual clinical exam may include causing presentation of a first task of the plurality of tasks, causing presentation of only the first task of the plurality of tasks, or causing presentation of two or more tasks of the plurality of tasks. In some examples, individual tasks of the plurality of tasks may be associated with individual conditions of the one or more conditions.

Figure 7:
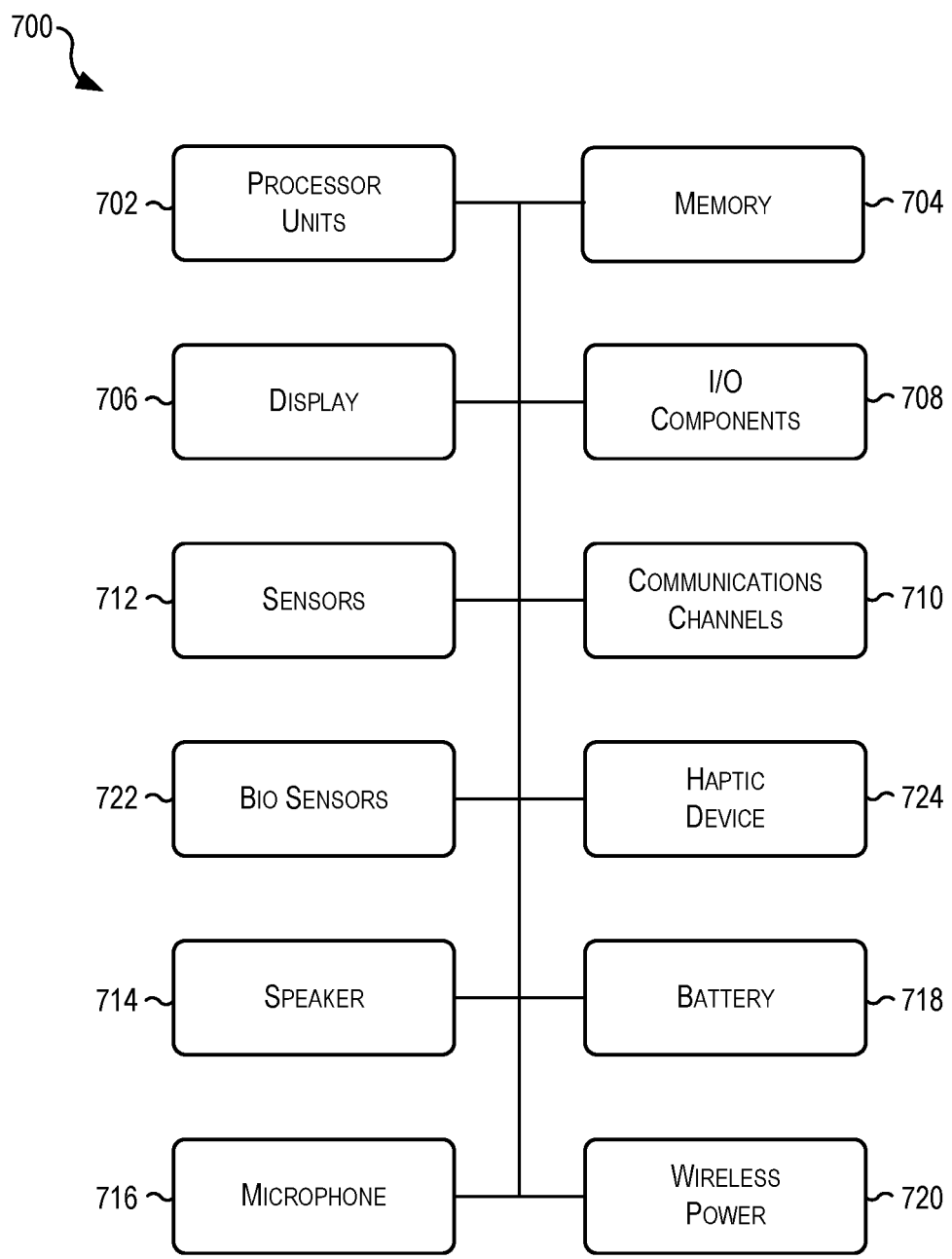
FIG. 7 illustrates an example block diagram of a user device for use in implementing techniques relating to triggering virtual clinical exams, according to at least one example.

FIG. 7 illustrates an example block diagram of a user device 700 for use in implementing techniques relating to triggering virtual clinical exams, according to at least one example. Examples described herein may take the form of, be incorporated in, or operate with a suitable wearable electronic device. One example of such a device is shown in FIG. 7 and takes the form of a wearable mechanism. As shown, the mechanism may be worn on a user's wrist and secured thereto by a band. The mechanism may have a variety of functions including, but not limited to: keeping time; monitoring a user's physiological signals and providing health-related information based at least in part on those signals; communicating (in a wired or wireless fashion) with other electronic devices, which may be different types of devices having different functionalities; providing alerts to a user, which may include audio, haptic, visual, and/or other sensory output, any or all of which may be synchronized with one another; visually depicting data on a display; gathering data from one or more sensors that may be used to initiate, control, or modify operations of the device; determining a location of a touch on a surface of the device and/or an amount of force exerted on the device, and using either or both as input; accepting voice input to control one or more functions; accepting tactile input to control one or more functions; and so on.

As shown in FIG. 7, the device 700 includes one or more processing units 702 that are configured to access a memory 704 having instructions stored thereon. Both the removable and non-removable memory 704 are examples of non-transitory computer-readable storage media. For example, non-transitory computer-readable storage media may include volatile or non-volatile, removable or non-removable media implemented in any method or technology for storage of information such as computer-readable instructions, data structures, program modules, or other data. The memory 704 is an example of non-transitory computer storage media. Additional types of computer storage media that may be present in the user device 700 may include, but are not limited to, PRAM, SRAM, DRAM, RAM, ROM, EEPROM, flash memory or other memory technology, CD-ROM, DVD or other optical storage, magnetic cassettes, magnetic tape, magnetic disk storage or other magnetic storage devices, or any other medium that can be used to store the desired information and that can be accessed by the user device 700. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The instructions or computer programs may be configured to perform one or more of the operations or functions described with respect to the device 700 (e.g., the exam engine 222). For example, the instructions may be configured to control or coordinate the operation of the various components of the device. Such components include, but are not limited to, display 706, one or more input/output (I/O) components 708, one or more communication channels 710, one or more sensors 712, a speaker 714, microphone 716, a battery 718, wireless power 720, bio sensors 722, and/or one or more haptic feedback devices 724. In some examples, the speaker and microphone may be combined into a single unit and/or may share a common port through a housing of the device.

The processing units 702 of FIG. 7 may be implemented as any electronic device capable of processing, receiving, or transmitting data or instructions. For example, the processing units 702 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

As shown in FIG. 7, the device 700 may also include one or more acoustic elements, including a speaker 714 and/or a microphone 716. The speaker 714 may include drive electronics or circuitry and may be configured to produce an audible sound or acoustic signal in response to a command or input. Similarly, the microphone 716 may also include drive electronics or circuitry and is configured to receive an audible sound or acoustic signal in response to a command or input. The speaker 714 and the microphone 716 may be acoustically coupled to a port or opening in the case that allows acoustic energy to pass, but may prevent the ingress of liquid and other debris.

Figure 8:
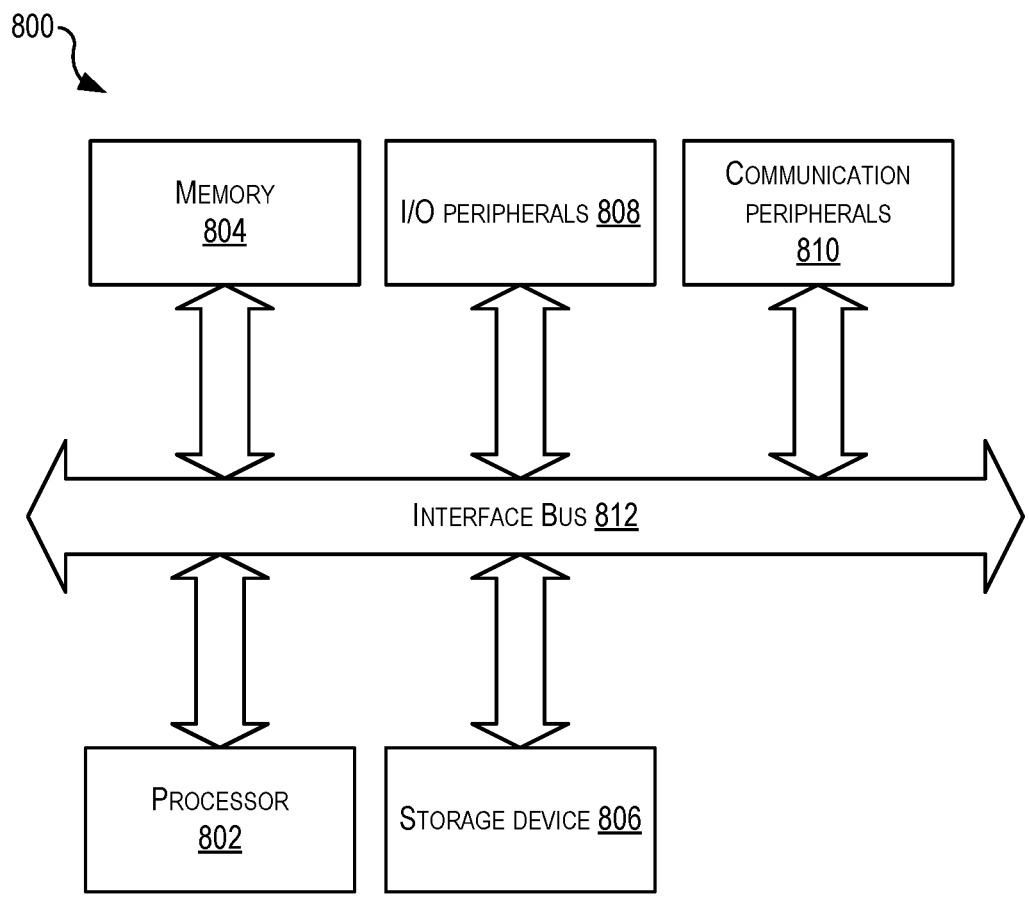
FIG. 8 illustrates an example system for implementing techniques relating to triggering virtual clinical exams, according to at least one example.

FIG. 8 illustrates examples of components of a computer system 800, according to at least one example. The computer system 800 may be a single computer, such as a user computing device, and/or can represent a distributed computing system, such as one or more server computing devices. The computer system 800 is an example of the computing device 106.

The computer system 800 may include at least a processor 802, a memory 804, a storage device 806, I/O peripherals 808, communication peripherals 810, and an interface bus 812. The interface bus 812 is configured to communicate, transmit, and transfer data, controls, and commands among the various components of the computer system 800. The memory 804 and the storage device 806 include computer-readable storage media, such as RAM; ROM; EEPROM; hard drives; CD-ROMs; optical storage devices; magnetic storage devices; electronic non-volatile computer storage, for example Flash® memory; and other tangible storage media. Any of such computer-readable storage media can be configured to store instructions or program codes embodying aspects of the disclosure. The memory 804 and the storage device 806 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the computer system 800.

Further, the memory 804 includes an operating system, programs, and applications. The processor 802 is configured to execute the stored instructions and includes, for example, a logical processing unit, a microprocessor, a DSP, and other processors. The memory 804 and/or the processor 802 can be virtualized and can be hosted within another computing system of, for example, a cloud network or a data center. The I/O peripherals 808 include user interfaces, such as a keyboard, screen (e.g., a touch screen), microphone, speaker, other I/O devices, and computing components, such as graphical processing units, serial ports, parallel ports, universal serial buses, and other I/O peripherals. The I/O peripherals 808 are connected to the processor 802 through any of the ports coupled to the interface bus 812. The communication peripherals 810 are configured to facilitate communication between the computer system 800 and other computing devices over a communications network and include, for example, a network interface controller, modem, wireless and wired interface cards, antenna, and other communication peripherals.

In the following, further examples are described to facilitate the understanding of the present disclosure.

Example 1. In this example, there is provided a computer-implemented method, including:
 receiving triggering information defining one or more conditions for triggering presentation of a virtual clinical exam at a user device;
 receiving, from one or more sensors, dynamic sensor data corresponding to multimodal physiological signals associated with a user of the user device;
 determining fulfillment of at least one condition of the one or more conditions based at least in part on a portion of the dynamic sensor data;
 causing presentation of the virtual clinical exam at the user device based at least in part on determining fulfillment of the at least one condition;
 receiving further data associated with the virtual clinical exam, wherein the further data includes at least one of further dynamic sensor data, further user-input data, or further electronic medical record data; and
 determining and outputting results of the virtual clinical exam based on the further data.

Example 2. In this example, there is provided a computer-implemented method of any of the preceding or subsequent examples, further including:
 generating a notification based at least in part on the results of the virtual clinical exam; and
 sending the notification to a healthcare provider associated with the user.

Example 3. In this example, there is provided a computer-implemented method of any of the preceding or subsequent examples, further including:
 updating an electronic health record associated with the user based at least in part on the results of the virtual clinical exam; and
 scheduling an appointment with a healthcare provider based at least in part on the results of the virtual clinical exam.

Example 4. In this example, there is provided a computer-implemented method of any of the preceding or subsequent examples,
 determining fulfillment of at least one other condition of the one or more conditions based at least in part on the dynamic sensor data; and
 determining a likelihood of success of the virtual clinical exam based at least in part on fulfillment of the at least one condition and the at least one other condition, wherein causing presentation of the virtual clinical exam includes causing presentation of the virtual clinical exam when the likelihood of success exceeds a threshold.

Example 5. In this example, there is provided a computer-implemented method of any of the preceding or subsequent examples, wherein the virtual clinical exam is a virtual motor exam that includes one or more tasks to test motor function.

Example 6. In this example, there is provided a computer-implemented method of any of the preceding or subsequent examples, wherein causing presentation of the virtual clinical exam includes causing presentation of a first task of the plurality of tasks, causing presentation of only the first task of the plurality of tasks, or causing presentation of two or more tasks of the plurality of tasks.

Example 7. In this example, there is provided a computer-implemented method of any of the preceding or subsequent examples, wherein individual tasks of the plurality of tasks are associated with individual conditions of the one or more conditions.

Example 8. In this example, there is provided a computer-implemented method of any of the preceding or subsequent examples, wherein determining the results of the virtual clinical exam includes sending information describing the portion of the dynamic sensor data and the at least one condition to a remote computing device and receiving one or more results from the remote computing device.

Example 9. In this example, there is provided a computer-implemented method of any of the preceding or subsequent examples, wherein receiving the triggering information includes receiving the triggering information from a remote computing device.

Example 10. In this example, there is provided a computer-implemented method of any of the preceding or subsequent examples, wherein the triggering information is based at least in part on historical scenarios in which the virtual clinical exam was presented to other user devices associated with other users.

Example 11. In this example, there is provided a computer-implemented method of any of the preceding or subsequent examples, wherein the virtual clinical exam tests at least one motor skill relating to a movement disorder.

Example 12. In this example, there is provided a computer-implemented method of any of the preceding or subsequent examples, wherein the at least one condition defines a value range for the dynamic sensor data.

Example 13. In this example, there is provided a computer-implemented method of any of the preceding or subsequent examples, wherein determining fulfillment of the at least one condition includes determining that at least one value of the dynamic sensor data is in the value range or outside of the value range.

Example 14. In this example, there is provided a computer-implemented method of any of the preceding or subsequent examples, wherein the one or more conditions comprise a plurality of value ranges including at least one value range for the dynamic sensor data and at least one value range for static data.

Example 15. In this example, there is provided a computer-implemented method of any of the preceding or subsequent examples, wherein the static data includes at least one of demographic data or health record data.

Example 16. In this example, there is provided a computer-implemented method of any of the preceding or subsequent examples, wherein the device is a wearable device that includes the one or more sensors.

Example 17. In this example, there is provided a computer-implemented method of any of the preceding or subsequent examples, wherein the one or more conditions are specific to the user of the user device.

Example 18. In this example, there is provided a non-transitory computer-readable storage device including computer-executable instructions that, when executed by a user device, cause the user device to perform operations including:
 receive triggering information defining one or more conditions for triggering presentation of a virtual clinical exam at the user device;
 receive, from one or more sensors, dynamic sensor data corresponding to multimodal physiological signals associated with a user of the user device;
 determine fulfillment of at least one condition of the one or more conditions based at least in part on a portion of the dynamic sensor data;
 cause presentation of the virtual clinical exam at the user device based at least in part on determining fulfillment of the at least one condition;
 receive further data associated with the virtual clinical exam, wherein the further data includes at least one of further dynamic sensor data, further user-input data, or further electronic medical record data; and
 determine and output results of the virtual clinical exam based on the further data.

Example 19. In this example, there is provided a user device, including:
 a memory for storing computer-executable instructions; and
 a processor configured to access the memory and execute the computer-executable instructions to at least:
  receive triggering information defining one or more conditions for triggering presentation of a virtual clinical exam at the user device;
  receive, from one or more sensors, dynamic sensor data corresponding to multimodal physiological signals associated with a user of the user device;
  determine fulfillment of at least one condition of the one or more conditions based at least in part on a portion of the dynamic sensor data;
  cause presentation of the virtual clinical exam at the user device based at least in part on determining fulfillment of the at least one condition;
  receive further data associated with the virtual clinical exam, wherein the further data includes at least one of further dynamic sensor data, further user-input data, or further electronic medical record data; and
  determine and output results of the virtual clinical exam based on the further data.

Example 20. In this example, there is provided a computer-implemented method, including:
 receiving, from a plurality of user devices, exam information corresponding to a plurality of virtual clinical exams performed by the plurality of user devices, the exam information identifying at least a virtual clinical exam type for each of the plurality of virtual clinical exams;
 receiving, from the plurality of user devices, dynamic sensor data corresponding to the plurality of virtual clinical exams, the dynamic sensor data collected by one or more sensors of the plurality of user devices;
 determining one or more conditions for triggering presentation of a particular type of virtual clinical exam based at least in part on the exam information and the dynamic sensor data; and
 providing the one or more conditions to a particular user device for use by the particular user device in triggering presentation of the particular type of virtual clinical exam at the particular user device.

Example 21. In this example, there is provided a computer-implemented method of any of the preceding or subsequent examples, further including training a machine-learning model using the exam information and the dynamic sensor data as inputs to the machine-learning model, and determining the one or more conditions based at least in part on the machine-learning model.

Example 22. In this example, there is provided a computer-implemented method of any of the preceding or subsequent examples, further including:
 receiving updated exam information associated with presentation of the particular type of virtual clinical exam at the particular user device;
 receiving updated dynamic sensor data associated with presentation of the particular type of virtual clinical exam at the particular user device; and
 updating the one or more conditions based at least in part on the updated exam information and the updated dynamic sensor data.

Example 23. In this example, there is provided a computer-implemented method of any of the preceding or subsequent examples, wherein the dynamic sensor data comprise raw sensor data.

Example 24. In this example, there is provided a computer-implemented method of any of the preceding or subsequent examples, wherein the exam information identifies at least beginning times and ending times for the plurality of virtual clinical exams.

Example 25. In this example, there is provided a computer-implemented method of any of the preceding or subsequent examples, wherein the plurality of virtual clinical exams are tailored to one or more movement disorders.

Example 26. In this example, there is provided a computer-implemented method of any of the preceding or subsequent examples, further including receiving static data including at least health record data or demographic data, and wherein determining the one or more conditions includes determining the one or more conditions based at least in part on the static data.

Example 27. In this example, there is provided a computer-implemented method of any of the preceding or subsequent examples, further including receiving user profile information corresponding to a particular user profile that is associated with the particular user device, wherein determining the one or more conditions includes determining the one or more conditions based at least in part on the user profile information.

Example 28. In this example, there is provided a computer-implemented method of any of the preceding or subsequent examples, wherein the one or more conditions define one or more value ranges for the dynamic sensor data.

Example 29. In this example, there is provided a non-transitory computer-readable storage device including computer-executable instructions that, when executed by a user device, cause the user device to perform operations including:
  receive, from a plurality of user devices, exam information corresponding to a plurality of virtual clinical exams performed by the plurality of user devices, the exam information identifying at least a virtual clinical exam type for each of the plurality of virtual clinical exams;
  receive, from the plurality of user devices, dynamic sensor data corresponding to the plurality of virtual clinical exams, the dynamic sensor data collected by one or more sensors of the plurality of user devices;
  determine one or more conditions for triggering presentation of a particular type of virtual clinical exam based at least in part on the exam information and the dynamic sensor data; and
  provide the one or more conditions to a particular user device for use by the particular user device in triggering presentation of the particular type of virtual clinical exam at the particular user device.

Example 30. In this example, there is provided a non-transitory computer-readable storage device of any of the preceding or subsequent examples, further including additional computer-executable instructions that, when executed by the user device, cause the user device to perform additional operations including train a machine-learning model using the exam information and the dynamic sensor data as inputs to the machine-learning model, and determine the one or more conditions based at least in part on the machine-learning model.

Example 31. In this example, there is provided a non-transitory computer-readable storage device of any of the preceding or subsequent examples, further including additional computer-executable instructions that, when executed by the user device, cause the user device to perform additional operations including:
  receive updated exam information associated with presentation of the particular type of virtual clinical exam at the particular user device;
  receive updated dynamic sensor data associated with presentation of the particular type of virtual clinical exam at the particular user device; and
  update the one or more conditions based at least in part on the updated exam information and the updated dynamic sensor data.

Example 32. In this example, there is provided a non-transitory computer-readable storage device of any of the preceding or subsequent examples, wherein the dynamic sensor data comprise raw sensor data.

Example 33. In this example, there is provided a non-transitory computer-readable storage device of any of the preceding or subsequent examples, wherein the exam information identifies at least beginning times and ending times for the plurality of virtual clinical exams.

Example 34. In this example, there is provided a non-transitory computer-readable storage device of any of the preceding or subsequent examples, wherein the plurality of virtual clinical exams are tailored to one or more movement disorders.

Example 35. In this example, there is provided a non-transitory computer-readable storage device of any of the preceding or subsequent examples, further including additional computer-executable instructions that, when executed by the user device, cause the user device to perform additional operations including receive static data including at least health record data or demographic data, and wherein determining the one or more conditions includes determining the one or more conditions based at least in part on the static data While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions, and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computing systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be reordered, combined, and/or broken into sub-blocks. Certain blocks or processes can be performed in parallel.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements, and/or steps are in any way required for one or more examples or that one or more examples necessarily include logic for deciding, with or without author input or prompting, whether these features, elements and/or steps are included or are to be performed in any particular example.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Use herein of the word "or" is intended to cover inclusive and exclusive OR conditions. In other words, "A or B or C" includes any or all of the following alternative combinations as appropriate for a particular usage: A alone; B alone; C alone; A and B only; A and C only; B and C only; and all three of A and B and C.

The use of the terms "a," "an," and "the" and similar referents in the context of describing the disclosed examples (especially in the context of the following claims) are to be construed to cover both the singular and the plural, unless otherwise indicated herein or clearly contradicted by context. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method, comprising:
    accessing, by a user device, one or more triggering conditions for presentation of a virtual clinical exam at the user device;
    establishing, by the user device, a network connection between the user device and one or more sensors, wherein the one or more sensors are associated with a user of the user device;
    receiving, by the user device from the one or more sensors, dynamic sensor data, wherein the one or more sensors collect the dynamic sensor data corresponding to multimodal physiological signals associated with the user of the user device;
    determining, by the user device, fulfillment of at least one triggering condition of the one or more triggering conditions based at least in part on a portion of the dynamic sensor data;
    causing, by the user device, presentation of the virtual clinical exam in a graphical user interface at the user device based at least in part on determining fulfillment of the at least one triggering condition;
    receiving, by the user device, further data during the virtual clinical exam, wherein the further data comprises at least one of further dynamic sensor data, further user-input data, or further electronic medical record data; and
    determining and outputting, by the user device, results of the virtual clinical exam based on the further data.

2. The computer-implemented method of claim 1, further comprising:
    generating a notification based at least in part on the results of the virtual clinical exam; and sending the notification to a healthcare provider associated with the user.

3. The computer-implemented method of claim 1, further comprising:
    updating an electronic health record associated with the user based at least in part on the results of the virtual clinical exam; and
    scheduling an appointment with a healthcare provider based at least in part on the results of the virtual clinical exam.

4. The computer-implemented method of claim 1, further comprising:
    determining fulfillment of at least one other triggering condition of the one or more triggering conditions based at least in part on the dynamic sensor data; and
    determining a likelihood of success of the virtual clinical exam based at least in part on fulfillment of the at least one triggering condition and the at least one other triggering condition, wherein causing presentation of the virtual clinical exam comprises causing presentation of the virtual clinical exam when the likelihood of success exceeds a threshold.

5. The computer-implemented method of claim 1, wherein the virtual clinical exam is a virtual motor exam that comprises a plurality of tasks to test motor function.

6. The computer-implemented method of claim 5, wherein causing presentation of the virtual clinical exam comprises causing presentation of a first task of the plurality of tasks, causing presentation of only the first task of the plurality of tasks, or causing presentation of two or more tasks of the plurality of tasks.

7. The computer-implemented method of claim 5, wherein individual tasks of the plurality of tasks are associated with individual conditions of the one or more conditions.

8. The computer-implemented method of claim 1, wherein determining the results of the virtual clinical exam comprises sending information describing the portion of the dynamic sensor data and the at least one triggering condition to a remote computing device and receiving one or more results from the remote computing device.

9. The computer-implemented method of claim 1, wherein receiving the one or more triggering conditions comprises receiving the one or more triggering conditions from a remote computing device.

10. The computer-implemented method of claim 1, wherein the one or more triggering conditions are based at least in part on historical scenarios in which the virtual clinical exam was presented to other user devices associated with other users.

11. The computer-implemented method of claim 1, wherein the virtual clinical exam tests at least one motor skill relating to a movement disorder.

12. The computer-implemented method of claim 1, wherein the at least one triggering condition defines a value range for the dynamic sensor data.

13. The computer-implemented method of claim 12, wherein determining fulfillment of the at least one triggering condition comprises determining that at least one value of the dynamic sensor data is in the value range or outside of the value range.

14. The computer-implemented method of claim 1, wherein the one or more triggering conditions comprise a plurality of value ranges including at least one value range for the dynamic sensor data and at least one value range for static data.

15. The computer-implemented method of claim 14, wherein the static data comprises at least one of demographic data or health record data.

16. The computer-implemented method of claim 1, wherein the user device is a wearable user device that comprises the one or more sensors.

17. The computer-implemented method of claim 1, wherein the one or more triggering conditions are specific to the user of the user device.

18. The computer-implemented method of claim 1, further comprising:
    prior to cause presentation of the virtual clinical exam, causing the one or more sensors to collect the dynamic sensor data at a first sampling rate; and
    during the virtual clinical exam, causing the one or more sensors to collect the dynamic sensor data at a second sampling rate.

19. A non-transitory computer-readable storage device comprising computer executable instructions that, when executed by a user device, cause the user device to perform operations comprising:
    receive one or more triggering conditions for presentation of a virtual clinical exam at the user device;
    establishing a network connection between the user device and one or more sensors, wherein the one or more sensors are associated with a user of the user device;
    receive, from the one or more sensors, dynamic sensor data, wherein the one or more sensors are configured to collect the dynamic sensor data corresponding to multimodal physiological signals associated with the user of the user device;
    determine fulfillment of at least one triggering condition of the one or more triggering conditions based at least in part on a portion of the dynamic sensor data;
    cause presentation of the virtual clinical exam in a graphical user interface at the user device based at least in part on determining fulfillment of the at least one triggering condition;
    receive further data during the virtual clinical exam, wherein the further data comprises at least one of further dynamic sensor data, further user-input data, or further electronic medical record data; and
    determine and output results of the virtual clinical exam based on the further data.

20. A system, comprising:
    a service provider server, a user device, and one or more sensors, wherein the user device is configured to establish a network connection with the one or more sensors,
    wherein the service provider server is configured to generate one or more triggering conditions for presenting a virtual clinical exam;
    wherein the one or more sensors are configured to be associated with a user of the user device and configured to collect dynamic sensor data corresponding to multimodal physiological signals associated with the user of the user device;
    wherein the user device comprises:
        a memory for storing computer-executable instructions; and
        a processor configured to access the memory and execute computer executable instructions to at least:
            receive from the service provider server one or more triggering conditions for presentation of a virtual clinical exam at the user device;
            receive, from the one or more sensors, the dynamic sensor data;

determine fulfillment of at least one triggering condition of the one or more triggering conditions based at least in part on a portion of the dynamic sensor data;

cause presentation of the virtual clinical exam in a graphical user interface at the user device based at least in part on determining fulfillment of the at least one triggering condition;

receive further data during the virtual clinical exam, wherein the further data comprises at least one of further dynamic sensor data, further user-input data, or further electronic medical record data; and determine and output results of the virtual clinical exam based on the further data.

* * * * *